(12) United States Patent
Foster et al.

(10) Patent No.: US 8,825,181 B2
(45) Date of Patent: Sep. 2, 2014

(54) LEAD CONDUCTOR WITH PITCH AND TORQUE CONTROL FOR MRI CONDITIONALLY SAFE USE

(75) Inventors: Arthur J. Foster, Centerville, MN (US); Neranjan Persaud, Brooklyn Park, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 13/156,531

(22) Filed: Jun. 9, 2011

(65) Prior Publication Data

US 2012/0053662 A1 Mar. 1, 2012

Related U.S. Application Data

(60) Provisional application No. 61/378,086, filed on Aug. 30, 2010.

(51) Int. Cl.
*A61N 1/00* (2006.01)
*A61N 1/05* (2006.01)
*A61N 1/08* (2006.01)

(52) U.S. Cl.
CPC ................................. *A61N 1/05* (2013.01); *A61N 2001/086* (2013.01)
USPC ............ 607/122; 607/115; 607/116; 607/119

(58) Field of Classification Search
USPC .................. 607/115, 116, 119, 122
See application file for complete search history.

(56) References Cited

U.S. PATENT DOCUMENTS

| | | | |
|---|---|---|---|
| 3,614,692 | A | 10/1971 | Rozelle et al. |
| 4,131,759 | A | 12/1978 | Felkel |
| 4,135,518 | A | 1/1979 | Dutcher |
| 4,404,125 | A | 9/1983 | Abolins et al. |
| 4,437,474 | A | 3/1984 | Peers-Trevarton |
| 4,484,586 | A | 11/1984 | McMickle et al. |
| 4,493,329 | A | 1/1985 | Crawford et al. |
| 4,643,203 | A | 2/1987 | Labbe |
| 4,869,970 | A | 9/1989 | Gulla et al. |
| 5,003,975 | A | 4/1991 | Hafelfinger et al. |

(Continued)

FOREIGN PATENT DOCUMENTS

| | | |
|---|---|---|
| CN | 1762510 A | 4/2006 |
| CN | 101039619 A | 9/2007 |

(Continued)

OTHER PUBLICATIONS

International Search Report and Written Opinion issued in PCT/US2012/055673, mailed Dec. 13, 2012, 10 pages.

(Continued)

*Primary Examiner* — Michael Kahelin
*Assistant Examiner* — Mallika D Fairchild
(74) *Attorney, Agent, or Firm* — Faegre Baker Daniels LLP

(57) ABSTRACT

A medical device lead includes an insulated lead body including at least one electrode, a helically coiled conductor electrically coupled to the at least one electrode, and one or more polymer coils formed coaxially with the helically coiled conductor. The helically coiled conductor includes a plurality of turns having a conductive coil pitch and including one or more conductive filars each having a conductive filar diameter. The one or more polymer coils provide at least about 25 μN·m of torque transmitting capacity along a length of the medical device lead.

20 Claims, 3 Drawing Sheets

(56) References Cited

U.S. PATENT DOCUMENTS

| | | |
|---|---|---|
| 5,056,516 A | 10/1991 | Spehr |
| 5,074,313 A | 12/1991 | Dahl et al. |
| 5,201,865 A | 4/1993 | Kuehn |
| 5,217,010 A | 6/1993 | Tsitlik et al. |
| 5,222,506 A | 6/1993 | Patrick et al. |
| 5,231,996 A | 8/1993 | Bardy et al. |
| 5,241,957 A | 9/1993 | Camp et al. |
| 5,243,911 A | 9/1993 | Dow et al. |
| 5,246,014 A | 9/1993 | Williams et al. |
| 5,324,322 A | 6/1994 | Grill, Jr. et al. |
| 5,330,522 A | 7/1994 | Kreyenhagen |
| 5,354,327 A | 10/1994 | Smits |
| 5,370,666 A | 12/1994 | Lindberg et al. |
| 5,378,234 A | 1/1995 | Hammerslag et al. |
| 5,387,199 A | 2/1995 | Siman et al. |
| 5,417,208 A | 5/1995 | Winkler |
| 5,425,755 A | 6/1995 | Doan |
| 5,456,707 A | 10/1995 | Giele |
| 5,476,485 A | 12/1995 | Weinberg et al. |
| 5,483,022 A | 1/1996 | Mar |
| 5,522,872 A | 6/1996 | Hoff |
| 5,522,875 A | 6/1996 | Gates et al. |
| 5,534,018 A | 7/1996 | Wahlstrand et al. |
| 5,545,205 A | 8/1996 | Schulte et al. |
| 5,549,646 A | 8/1996 | Katz et al. |
| 5,554,139 A | 9/1996 | Okajima |
| 5,574,249 A | 11/1996 | Lindsay |
| 5,584,873 A | 12/1996 | Shoberg et al. |
| 5,599,576 A | 2/1997 | Opolski |
| 5,609,622 A | 3/1997 | Soukup et al. |
| 5,618,208 A | 4/1997 | Crouse et al. |
| 5,727,552 A | 3/1998 | Ryan |
| 5,727,553 A | 3/1998 | Saad |
| 5,728,149 A | 3/1998 | Laske et al. |
| 5,755,742 A | 5/1998 | Schuelke et al. |
| 5,760,341 A | 6/1998 | Laske et al. |
| 5,766,227 A | 6/1998 | Nappholz et al. |
| 5,800,496 A | 9/1998 | Swoyer et al. |
| 5,810,887 A | 9/1998 | Accorti, Jr. et al. |
| 5,817,136 A | 10/1998 | Nappholz et al. |
| 5,824,026 A | 10/1998 | Diaz |
| 5,833,715 A | 11/1998 | Vachon et al. |
| 5,849,031 A | 12/1998 | Martinez et al. |
| 5,891,114 A | 4/1999 | Chien et al. |
| 5,891,179 A | 4/1999 | Er et al. |
| 5,935,159 A | 8/1999 | Cross, Jr. et al. |
| 5,957,966 A | 9/1999 | Schroeppel et al. |
| 5,957,970 A | 9/1999 | Shoberg et al. |
| 5,968,087 A | 10/1999 | Hess et al. |
| 6,016,447 A | 1/2000 | Juran et al. |
| 6,057,031 A | 5/2000 | Breme et al. |
| 6,078,840 A | 6/2000 | Stokes |
| 6,083,216 A | 7/2000 | Fischer, Sr. |
| 6,101,417 A | 8/2000 | Vogel et al. |
| 6,106,522 A | 8/2000 | Fleischman et al. |
| 6,141,593 A | 10/2000 | Patag |
| 6,143,013 A | 11/2000 | Samson et al. |
| 6,178,355 B1 | 1/2001 | Williams et al. |
| 6,192,280 B1 | 2/2001 | Sommer et al. |
| 6,208,881 B1 | 3/2001 | Champeau |
| 6,249,708 B1 | 6/2001 | Nelson et al. |
| 6,256,541 B1 | 7/2001 | Heil et al. |
| 6,259,954 B1 | 7/2001 | Conger et al. |
| 6,289,250 B1 | 9/2001 | Tsuboi et al. |
| 6,295,476 B1 | 9/2001 | Schaenzer |
| 6,304,784 B1 | 10/2001 | Allee et al. |
| 6,317,633 B1 | 11/2001 | Jorgenson et al. |
| 6,360,129 B1 | 3/2002 | Ley et al. |
| 6,400,992 B1 | 6/2002 | Borgersen et al. |
| 6,428,537 B1 | 8/2002 | Swanson et al. |
| 6,434,430 B2 | 8/2002 | Borgersen et al. |
| 6,456,888 B1 | 9/2002 | Skinner et al. |
| 6,493,591 B1 | 12/2002 | Stokes |
| 6,501,991 B1 | 12/2002 | Honeck et al. |
| 6,501,994 B1 | 12/2002 | Janke et al. |
| 6,510,345 B1 | 1/2003 | Van Bentem |
| 6,516,230 B2 | 2/2003 | Williams et al. |
| 6,526,321 B1 | 2/2003 | Spehr |
| 6,564,107 B1 | 5/2003 | Bodner et al. |
| 6,671,554 B2 | 12/2003 | Gibson et al. |
| 6,721,600 B2 | 4/2004 | Jorgenson et al. |
| 6,721,604 B1 | 4/2004 | Robinson et al. |
| 6,813,251 B1 | 11/2004 | Garney et al. |
| 6,850,803 B1 | 2/2005 | Jimenez et al. |
| 6,854,994 B2 | 2/2005 | Stein et al. |
| 6,866,044 B2 | 3/2005 | Bardy et al. |
| 6,906,256 B1 | 6/2005 | Wang |
| 6,909,256 B2 | 6/2005 | Wang |
| 6,920,361 B2 | 7/2005 | Williams |
| 6,925,334 B1 | 8/2005 | Salys |
| 6,949,929 B2 | 9/2005 | Gray et al. |
| 6,978,185 B2 * | 12/2005 | Osypka ...................... 607/122 |
| 6,993,373 B2 | 1/2006 | Vrijheid et al. |
| 6,999,818 B2 | 2/2006 | Stevenson et al. |
| 6,999,821 B2 | 2/2006 | Jenney et al. |
| 7,013,180 B2 | 3/2006 | Dublin et al. |
| 7,013,182 B1 | 3/2006 | Krishnan |
| 7,047,075 B2 | 5/2006 | Stubbs |
| 7,047,083 B2 | 5/2006 | Gunderson et al. |
| 7,050,855 B2 | 5/2006 | Zeijlemaker et al. |
| 7,113,827 B2 | 9/2006 | Silvestri et al. |
| 7,123,013 B2 | 10/2006 | Gray |
| 7,127,294 B1 | 10/2006 | Wang et al. |
| 7,135,978 B2 | 11/2006 | Gisselberg et al. |
| 7,138,582 B2 | 11/2006 | Lessar et al. |
| 7,158,837 B2 | 1/2007 | Osypka et al. |
| 7,174,219 B2 | 2/2007 | Wahlstrand et al. |
| 7,174,220 B1 | 2/2007 | Chitre et al. |
| 7,205,768 B2 | 4/2007 | Schulz et al. |
| 7,239,916 B2 | 7/2007 | Thompson et al. |
| 7,257,449 B2 | 8/2007 | Bodner |
| 7,289,851 B2 | 10/2007 | Gunderson et al. |
| 7,363,090 B2 | 4/2008 | Halperin et al. |
| 7,369,898 B1 | 5/2008 | Kroll et al. |
| 7,378,931 B2 | 5/2008 | Odahara et al. |
| 7,388,378 B2 | 6/2008 | Gray et al. |
| 7,389,148 B1 | 6/2008 | Morgan |
| 7,453,344 B2 | 11/2008 | Maeda et al. |
| 7,535,363 B2 | 5/2009 | Gisselberg et al. |
| 7,571,010 B2 | 8/2009 | Zarembo et al. |
| 7,610,101 B2 | 10/2009 | Wedan et al. |
| 7,630,761 B2 | 12/2009 | Salo et al. |
| 7,765,005 B2 | 7/2010 | Stevenson |
| 7,917,213 B2 | 3/2011 | Bulkes et al. |
| 7,953,499 B2 | 5/2011 | Knapp et al. |
| 7,986,999 B2 | 7/2011 | Wedan et al. |
| 8,103,360 B2 | 1/2012 | Foster |
| 8,145,324 B1 | 3/2012 | Stevenson et al. |
| 8,170,688 B2 | 5/2012 | Wedan et al. |
| 8,244,346 B2 | 8/2012 | Foster et al. |
| 8,255,055 B2 | 8/2012 | Ameri |
| 8,306,630 B2 | 11/2012 | Stubbs et al. |
| 8,332,050 B2 | 12/2012 | Perrey et al. |
| 8,335,572 B2 | 12/2012 | Ameri |
| 8,391,994 B2 | 3/2013 | Foster et al. |
| 8,401,671 B2 | 3/2013 | Wedan et al. |
| 2002/0065544 A1 | 5/2002 | Smits |
| 2002/0072769 A1 | 6/2002 | Silvian et al. |
| 2002/0111664 A1 | 8/2002 | Bartig et al. |
| 2002/0128689 A1 | 9/2002 | Connelly et al. |
| 2002/0144720 A1 | 10/2002 | Zahorik et al. |
| 2003/0028231 A1 | 2/2003 | Partridge et al. |
| 2003/0050680 A1 | 3/2003 | Gibson et al. |
| 2003/0063946 A1 | 4/2003 | Williams et al. |
| 2003/0083723 A1 | 5/2003 | Wilkinson et al. |
| 2003/0083726 A1 | 5/2003 | Zeijlemaker et al. |
| 2003/0092303 A1 | 5/2003 | Osypka |
| 2003/0093136 A1 | 5/2003 | Osypka et al. |
| 2003/0093138 A1 | 5/2003 | Osypka et al. |
| 2003/0139794 A1 | 7/2003 | Jenney et al. |
| 2003/0140931 A1 | 7/2003 | Zeijlemaker et al. |
| 2003/0144705 A1 | 7/2003 | Funke |
| 2003/0144716 A1 | 7/2003 | Reinke et al. |
| 2003/0144718 A1 | 7/2003 | Zeijlemaker |

(56) References Cited

U.S. PATENT DOCUMENTS

| | | | |
|---|---|---|---|
| 2003/0144719 A1 | 7/2003 | Zeijlemaker |
| 2003/0144720 A1 | 7/2003 | Villaseca et al. |
| 2003/0144721 A1 | 7/2003 | Villaseca et al. |
| 2003/0204217 A1 | 10/2003 | Greatbatch |
| 2004/0014355 A1 | 1/2004 | Osypka et al. |
| 2004/0064161 A1 | 4/2004 | Gunderson et al. |
| 2004/0064173 A1 | 4/2004 | Hine et al. |
| 2004/0064174 A1 | 4/2004 | Belden |
| 2004/0088033 A1 | 5/2004 | Smits et al. |
| 2004/0122490 A1 | 6/2004 | Reinke et al. |
| 2004/0153049 A1 | 8/2004 | Hewitt et al. |
| 2004/0162600 A1 | 8/2004 | Williams |
| 2004/0167442 A1 | 8/2004 | Shireman et al. |
| 2004/0172117 A1 | 9/2004 | Hill et al. |
| 2004/0193140 A1 | 9/2004 | Griffin et al. |
| 2004/0243210 A1 | 12/2004 | Morgan et al. |
| 2004/0267107 A1 | 12/2004 | Lessar et al. |
| 2005/0030322 A1 | 2/2005 | Gardos |
| 2005/0070972 A1 | 3/2005 | Wahlstrand et al. |
| 2005/0090886 A1 | 4/2005 | MacDonald et al. |
| 2005/0113676 A1 | 5/2005 | Weiner et al. |
| 2005/0113873 A1 | 5/2005 | Weiner et al. |
| 2005/0113876 A1 | 5/2005 | Weiner et al. |
| 2005/0136385 A1 | 6/2005 | Mann et al. |
| 2005/0177135 A1 | 8/2005 | Hildebrand et al. |
| 2005/0182471 A1 | 8/2005 | Wang |
| 2005/0197677 A1 | 9/2005 | Stevenson |
| 2005/0222642 A1 | 10/2005 | Przybyszewski et al. |
| 2005/0222656 A1 | 10/2005 | Wahlstrand et al. |
| 2005/0222657 A1 | 10/2005 | Wahlstrand et al. |
| 2005/0222658 A1 | 10/2005 | Hoegh et al. |
| 2005/0222659 A1 | 10/2005 | Olsen et al. |
| 2005/0246007 A1 | 11/2005 | Sommer et al. |
| 2005/0267556 A1 | 12/2005 | Shuros et al. |
| 2005/0272280 A1 | 12/2005 | Osypka |
| 2005/0283167 A1 | 12/2005 | Gray |
| 2006/0009819 A1 | 1/2006 | Przybyszewski |
| 2006/0030774 A1 | 2/2006 | Gray et al. |
| 2006/0037461 A1 | 2/2006 | Yasumura |
| 2006/0041293 A1 | 2/2006 | Mehdizadeh et al. |
| 2006/0041294 A1 | 2/2006 | Gray |
| 2006/0041296 A1 | 2/2006 | Bauer et al. |
| 2006/0089691 A1 | 4/2006 | Kaplan et al. |
| 2006/0089695 A1 | 4/2006 | Bolea et al. |
| 2006/0089696 A1 | 4/2006 | Olsen et al. |
| 2006/0093685 A1 | 5/2006 | Mower et al. |
| 2006/0105066 A1 | 5/2006 | Teague et al. |
| 2006/0106442 A1 | 5/2006 | Richardson et al. |
| 2006/0118758 A1 | 6/2006 | Wang et al. |
| 2006/0129043 A1 | 6/2006 | Ben-Jacob et al. |
| 2006/0167536 A1 | 7/2006 | Nygren et al. |
| 2006/0200218 A1 | 9/2006 | Wahlstrand |
| 2006/0229693 A1 | 10/2006 | Bauer et al. |
| 2006/0247747 A1 | 11/2006 | Olsen et al. |
| 2006/0247748 A1 | 11/2006 | Wahlstrand et al. |
| 2006/0252314 A1 | 11/2006 | Atalar et al. |
| 2006/0253180 A1 | 11/2006 | Zarembo et al. |
| 2006/0271138 A1 | 11/2006 | MacDonald |
| 2006/0293737 A1 | 12/2006 | Krishnan |
| 2007/0010702 A1 | 1/2007 | Wang et al. |
| 2007/0027532 A1 | 2/2007 | Wang et al. |
| 2007/0106332 A1 | 5/2007 | Denker et al. |
| 2007/0112398 A1 | 5/2007 | Stevenson et al. |
| 2007/0156205 A1 | 7/2007 | Larson et al. |
| 2007/0179577 A1 | 8/2007 | Marshall et al. |
| 2007/0179582 A1 | 8/2007 | Marshall et al. |
| 2007/0191914 A1 | 8/2007 | Stessman |
| 2007/0208383 A1 | 9/2007 | Williams |
| 2008/0009905 A1 | 1/2008 | Zeijlemaker |
| 2008/0033497 A1 | 2/2008 | Bulkes et al. |
| 2008/0039709 A1 | 2/2008 | Karmarkar |
| 2008/0049376 A1 | 2/2008 | Stevenson et al. |
| 2008/0051854 A1 | 2/2008 | Bulkes et al. |
| 2008/0057784 A1 | 3/2008 | Zarembo et al. |
| 2008/0058902 A1 | 3/2008 | Gray et al. |
| 2008/0125754 A1 | 5/2008 | Beer et al. |
| 2008/0129435 A1 | 6/2008 | Gray |
| 2008/0132985 A1 | 6/2008 | Wedan et al. |
| 2008/0132986 A1 | 6/2008 | Gray et al. |
| 2008/0140152 A1 | 6/2008 | Imran et al. |
| 2008/0147155 A1* | 6/2008 | Swoyer et al. ............... 607/116 |
| 2008/0154348 A1 | 6/2008 | Atalar et al. |
| 2008/0208290 A1 | 8/2008 | Phillips et al. |
| 2008/0243218 A1* | 10/2008 | Bottomley et al. ........... 607/116 |
| 2008/0262584 A1 | 10/2008 | Bottomley et al. |
| 2009/0005825 A1 | 1/2009 | MacDonald |
| 2009/0024180 A1 | 1/2009 | Kisker et al. |
| 2009/0024197 A1 | 1/2009 | Jensen |
| 2009/0099440 A1 | 4/2009 | Viohl |
| 2009/0099555 A1 | 4/2009 | Viohl et al. |
| 2009/0118610 A1 | 5/2009 | Karmarkar et al. |
| 2009/0149920 A1 | 6/2009 | Li et al. |
| 2009/0149933 A1 | 6/2009 | Ameri |
| 2009/0198314 A1 | 8/2009 | Foster et al. |
| 2009/0204171 A1 | 8/2009 | Ameri |
| 2009/0210022 A1 | 8/2009 | Powers |
| 2009/0270956 A1 | 10/2009 | Vase et al. |
| 2009/0281608 A1 | 11/2009 | Foster |
| 2010/0010602 A1 | 1/2010 | Wedan et al. |
| 2010/0016935 A1 | 1/2010 | Strandberg et al. |
| 2010/0103215 A1 | 4/2010 | Iriguchi |
| 2010/0106215 A1 | 4/2010 | Stubbs et al. |
| 2010/0114277 A1 | 5/2010 | Zhao et al. |
| 2010/0125320 A1 | 5/2010 | Polkinghorne et al. |
| 2010/0137928 A1 | 6/2010 | Duncan et al. |
| 2010/0174348 A1 | 7/2010 | Bulkes et al. |
| 2010/0234929 A1 | 9/2010 | Scheuermann |
| 2010/0249892 A1 | 9/2010 | Bulkes et al. |
| 2010/0331936 A1 | 12/2010 | Perrey et al. |
| 2011/0060394 A1 | 3/2011 | Poore |
| 2011/0079423 A1 | 4/2011 | Zhao et al. |
| 2011/0087299 A1 | 4/2011 | Ameri |
| 2011/0087302 A1 | 4/2011 | Ameri |
| 2011/0093054 A1 | 4/2011 | Ameri |
| 2011/0160805 A1 | 6/2011 | Erbstoeszer et al. |
| 2011/0160816 A1 | 6/2011 | Stubbs et al. |
| 2011/0160817 A1 | 6/2011 | Foster et al. |
| 2011/0160818 A1 | 6/2011 | Struve |
| 2011/0160828 A1 | 6/2011 | Foster et al. |
| 2011/0160829 A1 | 6/2011 | Foster et al. |
| 2011/0208280 A1 | 8/2011 | Li et al. |
| 2011/0218422 A1 | 9/2011 | Atalar et al. |
| 2011/0238146 A1 | 9/2011 | Wedan et al. |
| 2011/0288403 A1 | 11/2011 | Kondabatni et al. |
| 2012/0016451 A1 | 1/2012 | Struve et al. |
| 2012/0022356 A1 | 1/2012 | Olsen et al. |
| 2012/0035698 A1 | 2/2012 | Johnson et al. |
| 2012/0109270 A1 | 5/2012 | Foster |
| 2012/0143273 A1 | 6/2012 | Stubbs et al. |
| 2012/0161901 A1 | 6/2012 | Stevenson et al. |
| 2012/0179233 A1 | 7/2012 | Wedan et al. |
| 2012/0253340 A1 | 10/2012 | Stevenson et al. |
| 2012/0271394 A1 | 10/2012 | Foster et al. |
| 2013/0116764 A1 | 5/2013 | Walker et al. |
| 2013/0158641 A1 | 6/2013 | Foster et al. |
| 2013/0190849 A1 | 7/2013 | Perrey et al. |
| 2013/0190850 A1 | 7/2013 | Wedan et al. |
| 2013/0282093 A1 | 10/2013 | Walker et al. |
| 2014/0067030 A1 | 3/2014 | Walker et al. |

FOREIGN PATENT DOCUMENTS

| | | |
|---|---|---|
| EP | 0897997 B1 | 2/2003 |
| EP | 1594564 A1 | 11/2005 |
| EP | 1852810 B1 | 11/2007 |
| JP | 2004141679 A | 5/2004 |
| JP | 2005501673 A | 1/2005 |
| JP | 2005515852 A | 6/2005 |
| JP | 2005515854 A | 6/2005 |
| WO | WO9606655 A1 | 3/1996 |
| WO | WO03089045 A2 | 10/2003 |
| WO | WO2004073791 A1 | 9/2004 |
| WO | WO2006105066 A2 | 3/2006 |
| WO | WO2006093685 A1 | 9/2006 |

(56) References Cited

FOREIGN PATENT DOCUMENTS

| WO | WO2007047966 A2 | 4/2007 |
|---|---|---|
| WO | WO2007089986 A1 | 8/2007 |
| WO | WO2007118194 A2 | 10/2007 |
| WO | WO2008051122 A1 | 5/2008 |
| WO | WO2009137186 A1 | 11/2009 |
| WO | WO2010078552 A1 | 7/2010 |

OTHER PUBLICATIONS

Gray, Robert W. et al., "Simple design changes to wires to substantially reduce MRI-induced heating at 1.5 T: implications for implanted leads", Magnetic Resonance Imaging 23 (2005) 887-891.
International Search Report and Written Opinion issued in PCT/US2008/085518 on Oct. 29, 2009, 15 pages.
International Search Report and Written Opinion issued in PCT/US2009/032838, mailed May 4, 2009, 14 pages.
International Search Report and Written Opinion issued in PCT/US2009/038629, mailed Jun. 29, 2009, 11 pages.
International Search Report and Written Opinion issued in PCT/US2010/024062, mailed Sep. 27, 2010.
International Search Report and Written Opinion issued in PCT/US2010/033686 on Aug. 10, 2010, 12 pages.
International Search Report and Written Opinion issued in PCT/US2010/055130, mailed Mar. 10, 2011, 11 pages.
International Search Report and Written Opinion issued in PCT/US2010/055653, mailed Feb. 1, 2011, 14 pages.
Invitation to Pay Additional Fees and Partial Search Report, dated Aug. 17, 2009, issued in PCT/US2008/085533, 6 pages.
Invitation to Pay Additional Fees and Partial Search Report, issued in PCT/US2010/024062, mailed May 7, 2010.
International Search Report and Written Opinion issued in PCT/US2013/037432, mailed Nov. 19, 2013, 17 pages.
Partial International Search Report issued in PCT/US2013/013432, mailed Jul. 17, 2013, 6 pages.
Partial International Search Report issued in PCT/US2013/037432, mailed Jul. 17, 2013, 6 pages.
"High Voltage Engineering and Testing, 2nd Edition", edited by Hugh M. Ryan, Institution of Engineering and Technology, 2001, 15 pages.
Avalanche Breakdown, Wikipedia Article, captured Apr. 6, 2010, [http://en.wikipedia.org/wiki/Avalanche_breakdown].
Basso, Christophe, "SPICE Model Simulates Spark-Gap Arrestor", Electronics Design, Strategy, and News (EDN), Jul. 3, 1997, 4 pages.
Citel Inc., Data Sheet, BH Series 2 Electrode Miniature Gas Discharge Tube Surge Arrester—8mm, May 14, 2009, 2 pages.
Hayes, David L., Chapter 4, "Generator and Lead Selection" from book entitled "Cardiac Pacing and Defibrillation a Clinical Approach", John Wiley & Sons, (c) 2000 Mayo Foundation, p. 129-157.
International Search Report and Written Opinion issued in PCT/US2009/056843, mailed Dec. 29, 2009, 13 pages.
International Search Report and Written Opinion issued in PCT/US2010/048620, mailed Apr. 5, 2011, 10 pages.
International Search Report and Written Opinion issued in PCT/US2010/053223, mailed Dec. 27, 2010, 11 pages.
International Search Report and Written Opinion issued in PCT/US2011/052541, dated Mar. 9, 2012, 22 pages.
International Search Report and Written Opinion issued in PCT/US2013/057732, mailed Dec. 13, 2013, 11 pages.
Partial International Search Report issued in PCT/US2011/052541, mailed Dec. 6, 2011, 4 pages.
Static Spark Gap Analysis, captured Dec. 24, 2002, [http;//www.richieburnett.co.uk/static.html].

\* cited by examiner

LEAD CONDUCTOR WITH PITCH AND TORQUE CONTROL FOR MRI CONDITIONALLY SAFE USE

CROSS-REFERENCE TO RELATED APPLICATION(S)

This application claims priority to Provisional Application No. 61/378,086, filed Aug. 30, 2010, which is herein incorporated by reference in its entirety.

TECHNICAL FIELD

The present invention relates to implantable medical devices. More particularly, the present invention relates to a medical device lead including one or more polymer filars or threads that are coiled around one or more conductive coils.

BACKGROUND

Implantable medical devices for treating a variety of medical conditions with electrical stimuli are well known. Implantable medical devices generally include a medical electrical lead for delivering an electrical stimulus to a targeted site within a patient's body such as, for example, a patient's heart or nervous system. Such leads generally have an elongated, flexible insulating body, one or more inner conductors extending through lumens formed in the body and one or more exposed electrodes connected to the distal ends of the conductors.

Leads may be introduced into the patient's vasculature at a venous access site and transvenously guided through veins to the sites where the lead electrodes will be implanted or otherwise contact tissue at the targeted therapy site. A pulse generator attached to the proximal ends of the conductors delivers an electrical stimulus therapy to the targeted site via the one or more conductors.

SUMMARY

Discussed herein are various conductor configurations for implantable medical electrical leads including a conductive coil with one or more polymer coils wound coaxially with the conductive coil, as well as medical electrical leads including such conductor configurations In Example 1, a medical device lead includes an insulated lead body including at least one electrode, a helically coiled conductor electrically coupled to the at least one electrode, and one or more polymer coils. The helically coiled conductor includes a plurality of turns having a conductive coil pitch and including one or more conductive filars each having a conductive filar diameter. The one or more polymer coils each include one or more polymer filars formed coaxially about the helically coiled conductor to provide at least about 25 µN·m of torque along a length of the medical device lead.

In Example 2, the medical device lead according to Example 1, wherein the helically coil conductor is unifilar, and wherein the conductive coil pitch is one to about two times the conductive filar diameter.

In Example 3, the medical device lead according to either Example 1 or 2, wherein the one or more polymer coils each have a polymer coil pitch, and wherein the polymer coil pitch is less than or equal to the conductive coil pitch.

In Example 4, the medical device lead according to any of Examples 1-3, wherein the one or more polymer filars each has a polymer filar diameter, and wherein the polymer filar diameter is less than or equal to the conductive filar diameter.

In Example 5, the medical device lead according to any of Examples 1-4, wherein the one or more polymer filars of at least one of the one or more polymer coils are wound in a direction opposite the one or more conductive filars.

In Example 6, the medical device lead according to any of Examples 1-5, wherein the one or more polymer coils comprises two polymer coils wound in opposite directions.

In Example 7, the medical device lead of any of Examples 1-6, wherein the one or more polymer coils are comprised of a material selected from the group consisting of expanded polytetrafluoroethylene (ePTFE), layered ePTFE, polytetrafluoroethylene (PTFE), polyethylene terephthalate (PETE), ethylene/tetrafluoroethylene copolymer (ETFE), fluorinated ethylene propylene (FEP), polyether ether ketone (PEEK), polyamides, polyimides, para-aramid synthetic fibers, and polyurethane.

In Example 8, a medical device lead includes an insulated lead body including at least one electrode, a helically coiled conductor electrically coupled to the at least one electrode, and one or more polymer coils. The helically coiled conductor includes a plurality of turns having a coil pitch and an outer diameter and including one or more conductive filars each having a filar diameter. The coil pitch and outer diameter are selected based on the filar diameter to minimize heating of the helically coiled conductor in the presence of an MRI field. The one or more polymer coils each include one or more polymer filars formed coaxially about the helically coiled conductor to increase a torque transmitting capacity of the helically coiled conductor.

In Example 9, the medical device lead according to Example 8, wherein the helically coil conductor is unifilar, and wherein the coil pitch is one to about two times the filar diameter.

In Example 10, the medical device lead according to either Example 8 or 9, wherein the outer diameter is at least 4.5 times the coil pitch.

In Example 11, the medical device lead according to any of Examples 8-10, wherein the one or more polymer coils each have a polymer coil pitch, and wherein the polymer coil pitch is less than or equal to the conductive coil pitch.

In Example 12, the medical device lead according to any of Examples 8-11, wherein the one or more polymer filars each has a polymer filar diameter, and wherein the polymer filar diameter is less than or equal to the conductive filar diameter.

In Example 13, the medical device lead according to any of Examples 8-12, wherein the one or more polymer filars of at least one of the one or more polymer coils are wound in a direction opposite the one or more conductive filars.

In Example 14, the medical device lead according to any of Examples 8-13, wherein the one or more polymer coils comprises two polymer coils wound in opposite directions.

In Example 15, a conductor assembly for a medical device lead includes a helically coiled conductor and one or more polymer filars formed coaxially about the helically coiled conductor to increase a torque transmitting capacity of the helically coiled conductor. The helically coiled conductor includes a plurality of turns having a conductive coil pitch and including one or more conductive filars each having a conductive filar diameter.

In Example 16, the conductor assembly according to Example 15, wherein the helically coil conductor is unifilar, and wherein the conductive coil pitch is one to about two times the conductive filar diameter.

In Example 17, the conductor assembly according to either Example 15 or 16, wherein the one or more polymer coils each have a polymer coil pitch, and wherein the polymer coil pitch is less than or equal to the conductive coil pitch.

In Example 18, the conductor assembly according to any of Examples 15-17, wherein the one or more polymer filars each has a polymer filar diameter, and wherein the polymer filar diameter is less than or equal to the conductive filar diameter.

In Example 19, the conductor assembly according to any of Examples 15-18, wherein the one or more polymer filars of at least one of the one or more polymer coils are wound in a direction opposite the one or more conductive filars.

In Example 20, the conductor assembly according to any of Examples 15-19, wherein the one or more polymer coils comprises two polymer coils wound in opposite directions.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
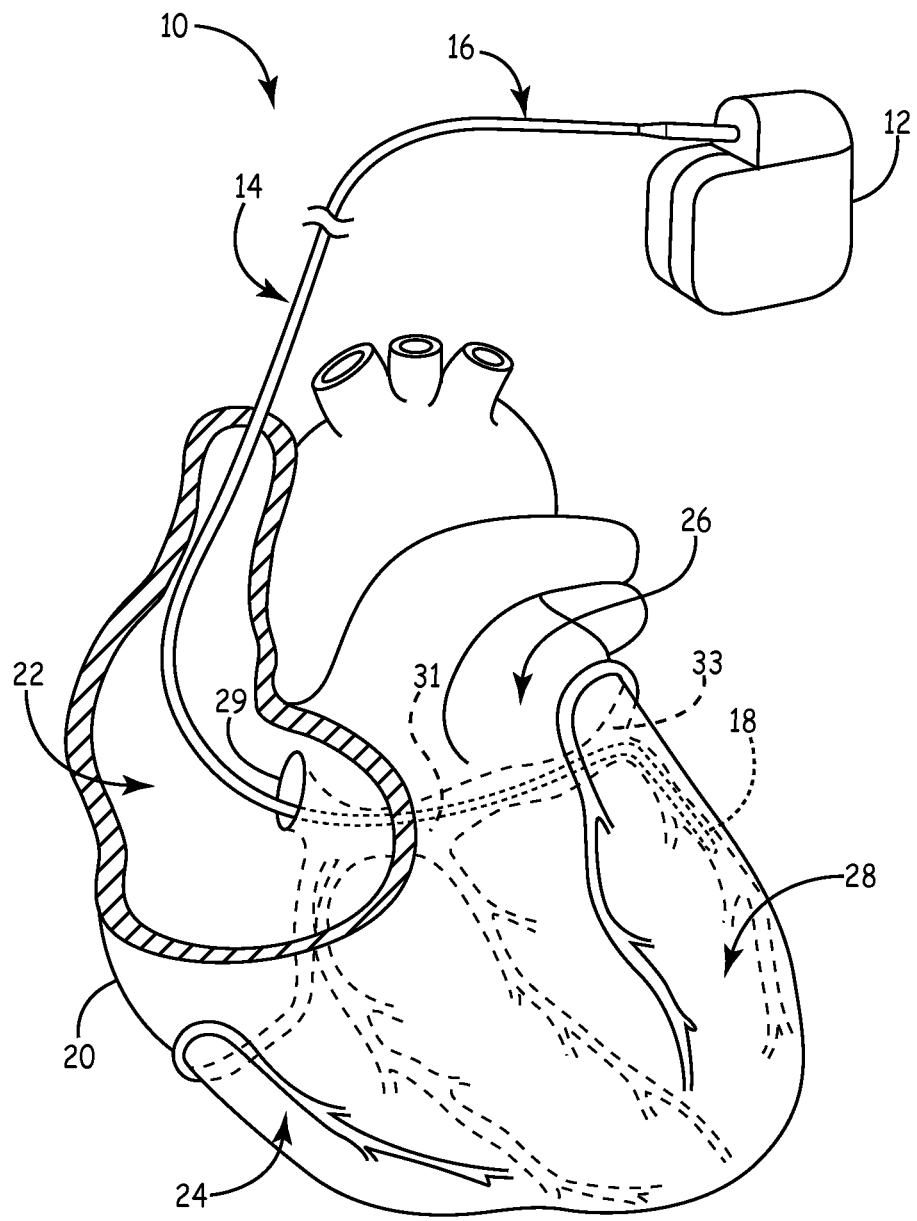
FIG. 1 is a schematic view of a cardiac rhythm management system including a pulse generator coupled to a lead deployed in a patient's heart.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 is a schematic view of a cardiac rhythm management system 10 including an implantable medical device (IMD) 12 with a lead 14 having a proximal end 16 and a distal end 18. In one embodiment, the IMD 12 includes a pulse generator such as a pacemaker or a defibrillator. The IMD 12 can be implanted subcutaneously within the body, typically at a location such as in the patient's chest or abdomen, although other implantation locations are possible. The proximal end 16 of the lead 14 can be coupled to or formed integrally with the IMD 12. The distal end 18 of the lead 14, in turn, can be implanted at a desired location in or near the heart 20.

As shown in FIG. 1, a distal portion of the lead 14 is disposed in a patient's heart 20, which includes a right atrium 22, a right ventricle 24, a left atrium 26, and a left ventricle 28. In the embodiment illustrated in FIG. 1, the distal end 18 of the lead 14 is transvenously guided through the right atrium 22, through the coronary sinus ostium 29, and into a branch of the coronary sinus 31 or the great cardiac vein 33. The illustrated position of the lead 14 can be used for sensing or for delivering pacing and/or defibrillation energy to the left side of the heart 20, or to treat arrhythmias or other cardiac disorders requiring therapy delivered to the left side of the heart 20. Additionally, it will be appreciated that the lead 14 can also be used to provide treatment in other regions of the heart 20 (e.g., the right ventricle 24).

Although the illustrative embodiment depicts only a single implanted lead 14, it should be understood that multiple leads can be utilized so as to electrically stimulate other areas of the heart 20. In some embodiments, for example, the distal end of a second lead (not shown) may be implanted in the right atrium 22, and/or the distal end of a third lead (not shown) may be implanted in the right ventricle 24. Other types of leads such as epicardial leads may also be utilized in addition to, or in lieu of, the lead 14 depicted in FIG. 1.

During operation, the lead 14 can be configured to convey electrical signals between the IMD 12 and the heart 20. For example, in those embodiments where the IMD 12 is a pacemaker, the lead 14 can be utilized to deliver electrical stimuli for pacing the heart 20. In those embodiments where the IMD 12 is an implantable cardiac defibrillator, the lead 14 can be utilized to deliver electric shocks to the heart 20 in response to an event such as a heart attack or arrhythmia. In some embodiments, the IMD 12 includes both pacing and defibrillation capabilities.

The electrical signals are carried between the IMD 12 and electrodes at the distal end 18 by one or more conductors extending through the lead 14. The one or more conductors are electrically coupled to a connector suitable for interfacing with the IMD 12 at the proximal end 16 of the lead 14, and to one or more electrodes at the distal end 18. According to the present disclosure, the one or more conductors can be helically coiled including a plurality of turns having a coil pitch and an outer diameter and a filar diameter. In some embodiments, the one or more conductors can be unifilar. In other embodiments, the one or more conductors can be multifilar. The coil pitch and outer diameter may be selected based on the filar diameter to minimize effects of magnetic resonance imaging (MRI) scans on the functionality and operation of the lead 14. One or more polymer coils can be formed about the helically coiled one or more conductors to increase the torque transmitting capacity, tensile strength, and elongation characteristics of the coil assembly. The one or more polymer coils can also be configured to maintain the pitch of the helically coiled conductor.

Figure 2A:
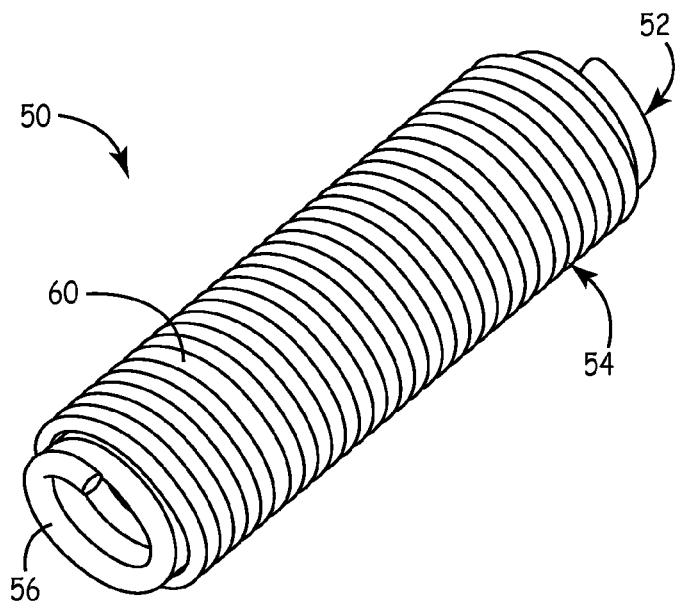
FIG. 2A is a perspective view of a conductor assembly including a conductive coil and a coaxial polymer coil according to an embodiment of the present invention.
Figure 2B:
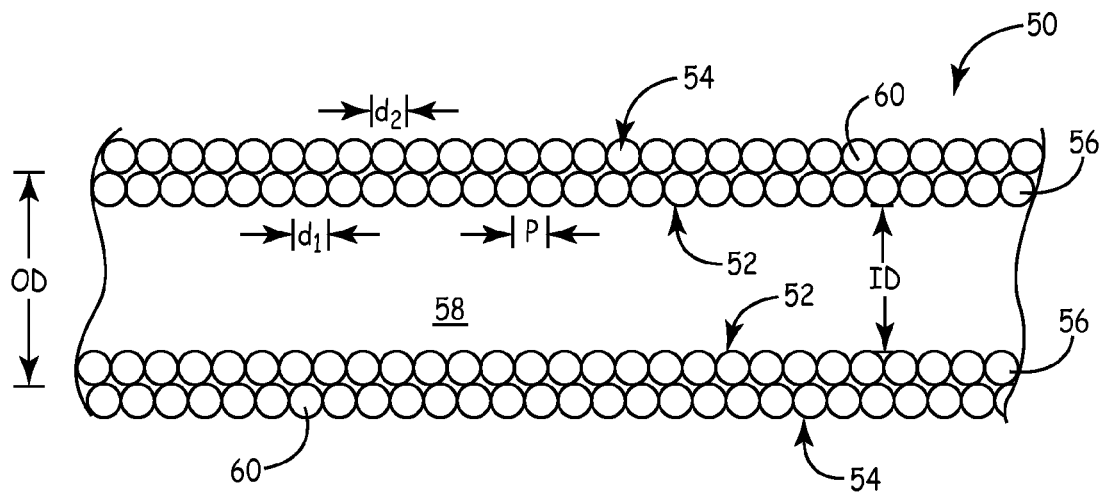
FIG. 2B is a cross-sectional view of the conductor assembly shown in FIG. 2A.

FIG. 2A is a perspective view, and FIG. 2B is a cross-sectional view, of a conductor assembly 50 according to embodiments of the present disclosure. The conductor assembly 50 can extend through the interior of the lead 14 and include a coil 52 and a polymer coil 54. The coil 52 can be coupled to the IMD 12 via a connector at the proximal end 16 of the lead 14 and to one or more electrodes at the distal end 18 of the lead 14. While a single coil 52 is shown in FIG. 2A and FIG. 2B, the conductor assembly 50 can be configured to include multiple coaxial and/or co-radial coils 52 each capable of delivering signals between the IMD 12 and the electrodes at the distal end 18.

In the embodiment shown, the coil 52 includes a single filar 56 that is helically wound around a longitudinal axis of the conductor assembly 50. In other embodiments, the coil 52 includes two or more filars 56. The filar 56 can have a diameter $d_1$. A lumen 58 extends through the center of the coil 52 and is suitable for receiving a tool to deliver the lead 14, such as a guidewire or stent. The coil 52 includes a plurality of turns having an outer diameter OD and an inner diameter ID. The coil 52 also can have a coil pitch p that extends from the center of a turn of the coil 52 to the center of an adjacent turn of the coil 52.

Exposure of the lead 14 to magnetic resonance imaging (MRI) fields can result in localized heating of the electrodes at the distal end 18 due to excitation of the lead conductors (e.g., coil 52). Conductors with high inductance (>1 µH) are more resistant to excitation in MRI fields. The inductance of the conductor is determined by its geometric properties, including whether the conductor is straight or coiled. For a coiled or wound conductor, such as the coil 52, several parameters influence its inductance, including the coil pitch p, the outer diameter OD, the cross-sectional area of the coil 52, and the number of filars comprising the coil. Thus, the dimensions of the coil 52 may be selected to minimize the effects of magnetic resonance imaging (MRI) fields on the performance and response of the lead 14. For example, for a conductor assembly 50 as shown including a single, unifilar coil 52, a coil pitch p in the range of one to about two times the filar diameter $d_1$, and an outer diameter OD at least about 4.5 times the coil pitch p can increase the inductance of the coil sufficiently to minimize the energy picked up by the coil 52, due to exposure to MRI fields.

Table 1 below provides example dimensions for the coil 52 to minimize electrode heating caused by MRI fields. The listed dimensions are for a coil 52 having a length (extending from the connector to the distal end 18) in the range of about 450 mm to about 600 mm.

TABLE 1

| Filar Diameter (d) (inch) | Coil Pitch (p) (inch) | Coil Outer Diameter (OD) (inch) |
|---|---|---|
| 0.0005 | 0.0005-0.0008 | 0.002 |
| 0.001 | 0.001-0.002 | 0.004 |
| 0.002 | 0.002-0.003 | 0.009 |
| 0.003 | 0.003-0.004 | 0.013 |
| 0.004 | 0.004-0.005 | 0.020 |
| 0.005 | 0.005-0.007 | 0.022 |
| 0.006 | 0.006-0.008 | 0.027 |
| 0.007 | 0.007-0.009 | 0.031 |
| 0.008 | 0.008-0.010 | 0.036 |
| 0.009 | 0.009-0.011 | 0.040 |
| 0.010 | 0.010-0.012 | 0.045 |
| 0.011 | 0.011-0.013 | 0.049 |

These dimensions are suitable for a conductor assembly 50 including a single, unifilar coil 52. The listed dimensions for the filar diameter $d_1$, coil pitch p, and coil outer diameter OD are only by way of example, and other dimensions that reduce electrode heating due to MRI fields to suitable levels are also contemplated. In addition, for embodiments of the conductor assembly 50 including multiple coaxial unifilar coil, these dimensions may change to account for the interaction of the coils with each other in the presence of an MRI field.

The coil 52 with a small diameter OD and having a small pitch p may be prone to damage during construction and use. For example, in active fixation leads, the coil 52 is intended to rotate relative to the lead body and drive torque to extend the fixation helix into tissue of the heart 20. Unifilar coils, such as coil 52, often do not transmit torque well, and the forces typically encountered by the lead 14 can cause the coil 52 to experience stress concentrations in portions of the coil 52, which can lead to premature fatigue of the coil 52. In order to improve the torque transmitting capacity of the coil 52, as well as to maintain the integrity of the coil pitch p, a polymer coil 54 can be formed around the coil 52.

The polymer coil 54 may be formed over the conductive coil 52 such that the polymer coil 54 is adjacent to or abutted against the conductive coil 52. The polymer coil 54 can include one or more polymeric filars 60 that are closely wound to form the polymer coil 54. In some embodiments, the polymer coil 54 can be wound to have a pitch substantially similar to the pitch p of the conductive coil 52. In other embodiments, the polymer coil 54 can be wound with a pitch different than the pitch p of the conductive coil 52. The polymer coil 54 may also have a pitch that varies along the length of the lead 14.

The polymer coil 54 can have a diameter $d_2$. In some embodiments, the diameter $d_2$ of the polymer coil 54 can be about equal to the diameter $d_1$ of the conductive coil 52. In other embodiments, the diameter $d_2$ can be less than the diameter $d_1$. In still further embodiments, the diameter $d_2$ can be greater than the diameter $d_1$.

The polymer coil 54 can increase the torque transmission capacity of the conductor assembly 50 and maintain the coil pitch p of the coil 52, while still allowing the conductor assembly 50 to sufficiently flex during use. The torque transmission capacity of the conductor assembly 50 refers to the maximum torque carrying capability of the conductor assembly 50. For example, in embodiments in which the conductor assembly 50 is rotated to actuate a distal mechanism (e.g., a fixation assembly), the conductor assembly 50 provides sufficient torque transmission capacity to turn the distal mechanism. In some embodiments, the polymer coil 54 can be configured to provide at least about 25 micronewton-meters (µN·m) of torque transmitting capacity over the length of the lead 14. In addition, the polymer coil 54 may be configured to maintain proper spacing of the coil turns with respect to each other. In some embodiments, the turns of the polymer coil 54 are at least partially disposed in the valleys or spaces between the turns of the conductive coil 52. The polymer coil 54 may be wound in a direction that increases the torque carrying capability of the conductive coil 52 in one or both directions. In some embodiments, the polymer coil 54 can be wound in the same direction as the conductive coil 52. In other embodiments, the polymer coil 54 can be wound in a direction opposite of the conductive coil 52.

In some embodiments, the polymer coil 54 may be configured to increase the torque-carrying capacity of a curved or tortuous section of the lead 14. For example, in a J-shaped lead, the lead has a sharp bend at the location of the J-shaped portion. The material, wind direction, and pitch of the polymer coil 54 may be selected to increase the torque carrying capacity of the conductive assembly 50 at the sharp bend in the J-shaped portion to minimize the potential for damage to the conductive coil 52 in this portion.

In some embodiments, the polymer coil 54 is made of a polymeric biocompatible material. Example materials that may be used for the polymer coil 54 include, but are not limited to, expanded polytetrafluoroethylene (ePTFE), layered ePTFE, polytetrafluoroethylene (PTFE), polyethylene terephthalate (PETE), ethylene/tetrafluoroethylene copolymer (ETFE), fluorinated ethylene propylene (FEP), polyether ether ketone (PEEK), polyamides, polyimides, para-aramid synthetic fibers, and polyurethane.

The polymer coil 54 may be adhered to portions of the coil 52 to prevent the polymer coil 54 from becoming detached from the coil 52. This may be accomplished by applying an adhesive material to the coil 52 prior to winding the polymer coil 54 thereon. However, in some cases, the material used for the polymer coil 54 does not adhere well to the material used for the coil 52. In order to assure good adhesion, the coil 52 may be coated with a material that bonds well with the polymer coil 54. For example, the filar 56 may be coated in a suitable polymer prior to coiling the filar 56 into coil 52.

Alternatively, the coil 52 may be etched, such as via laser etching, with a pattern that allows for good bonding with the polymer coil 54.

Figure 3A:
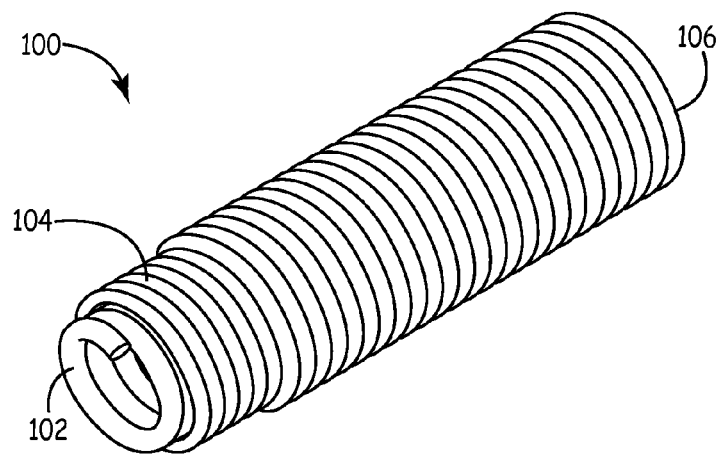
FIG. 3A is a perspective view of a conductor assembly including a conductive coil and a plurality of coaxial polymer coils according to another embodiment of the present invention.
Figure 3B:
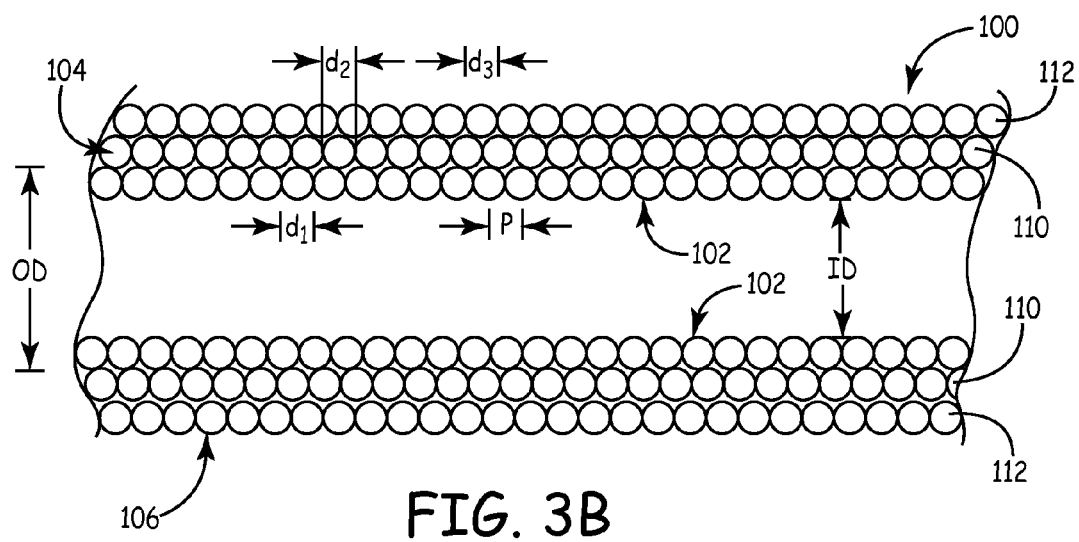
FIG. 3B is a cross-sectional view of the conductor assembly shown in FIG. 3A.

FIG. 3A is a perspective view, and FIG. 3B is a cross-sectional view of a conductor assembly 100 according to another embodiment of the present disclosure. The conductor assembly 100 can extend through the interior of the lead 14 and include a coil 102, first polymer coil 104, and second polymer coil 106. The coil 102 can be coupled to the IMD 12 via a connector at the proximal end 16 of the lead 14 and to one or more electrodes at the distal end 18 of the lead 14 (FIG. 1). The coil 102 may have properties, configurations, and characteristics substantially similar to conductive coil 52 discussed herein. While a single coil 102 is shown in FIG. 3A and FIG. 3B, the conductor assembly 100 can be configured to include multiple coaxial and/or co-radial coils 102 each capable of delivering signals between the IMD 12 and the electrodes at the distal end 18. In addition, while two polymer coils 104, 106 are shown, the conductor assembly 100 may include additional polymer coils.

The polymer coils 104, 106 may be formed over the conductive coil 102 such that the polymer coil 104 is adjacent to or abutted against the conductive coil 102, and the polymer coil 106 is adjacent to or abutted against the polymer coil 104. The polymer coil 104 can include one or more polymeric filars 110, and the polymer coil 106 can include one or more polymeric filars 112. In some embodiments, the polymer coils 104 and/or 106 can be wound to have a pitch substantially similar to the pitch p of the conductive coil 102. In other embodiments, the polymer coils 104 and/or 106 can be wound with a pitch different than the pitch p of the conductive coil 102. The polymer coils 104 and/or 106 may also have a pitch that varies along the length of the lead 14.

The first polymer coil 104 can have a diameter $d_2$ and the second polymer coil 106 can have a diameter $d_3$. In some embodiments, the diameter $d_2$ of the first polymer coil 104 and the diameter $d_3$ of the second polymer coil 106 can be about equal to the diameter $d_1$ of the conductive coil 102. In other embodiments, the diameter $d_2$ and/or diameter $d_3$ can be less than the diameter $d_1$. In still further embodiments, the diameter $d_2$ and/or diameter $d_3$ can be greater than the diameter $d_1$.

The polymer coils 104, 106 can increase the torque transmission capacity and maintain the coil pitch p of the coil 102, while still allowing the conductor assembly 100 to sufficiently flex during use. In some embodiments, the polymer coils 104, 106 can be configured to provide at least about 25 μN·m of torque transmitting capacity over the length of the lead 14. In addition, the polymer coils 104, 106 may be configured to maintain proper spacing of the coil turns with respect to each other. The polymer coils 104, 106 may be wound in directions that increase the torque carrying capability of the conductive coil 102 in one or both directions. In some embodiments, the first polymer coil 104 can be wound in the opposite direction as the conductive coil 102 and the second polymer coil 106 can be wound in the same direction as the conductive coil 102 and opposite direction of the first polymer coil 104. In other embodiments, the first polymer coil 104 can be wound in the same direction as the conductive coil 102 and the second polymer coil 106 can be wound in the opposite direction as the conductive coil 102. In further embodiments, the polymer coils 104, 106 can be wound in the same direction, and in the same or opposite direction as the conductive coil 102. In some embodiments, the polymer coils 104, 106 may be configured to increase the torque-carrying capacity of a curved or tortuous section of the lead 14.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A medical device lead comprising:
   an insulated lead body including at least one electrode;
   a helical conductor coil electrically coupled to the at least one electrode, the helical conductor coil having a circumference and including a plurality of turns having a conductive coil pitch, the helical conductor coil helically wound from one or more conductive filars each having a conductive filar diameter; and
   one or more polymer coils, each polymer coil extending over the helical conductor coil and completely around the entire circumference of the helical conductor coil, each polymer coil formed by one or more helically wound polymer filars disposed coaxially around and abutted against the circumference of the conductor coil, wherein the one or more polymer coils are configured to provide at least about 25 μN·m of torque transmitting capacity along a length of the medical device lead.

2. The medical device lead of claim 1, wherein the helical conductor coil is unifilar, and wherein the conductive coil pitch is one to about two times the conductive filar diameter.

3. The medical device lead of claim 1, wherein the one or more polymer coils each have a polymer coil pitch, and wherein the polymer coil pitch is less than or equal to the conductive coil pitch.

4. The medical device lead of claim 1, wherein the one or more polymer filars each has a polymer filar diameter, and wherein the polymer filar diameter is less than or equal to the conductive filar diameter.

5. The medical device lead of claim 1, wherein the one or more polymer filars of at least one of the one or more polymer coils are wound in a direction opposite the one or more conductive filars.

6. The medical device lead of claim 1, wherein the one or more polymer coils comprises two polymer coils wound in opposite directions.

7. The medical device lead of claim 1, wherein the one or more polymer coils are comprised of a material selected from the group consisting of expanded polytetrafluoroethylene (ePTFE), layered ePTFE, polytetrafluoroethylene (PTFE), polyethylene terephthalate (PETE), ethylene/tetrafluoroethylene copolymer (ETFE), fluorinated ethylene propylene (FEP), polyether ether ketone (PEEK), polyamides, polyimides, para-aramid synthetic fibers, and polyurethane.

8. A medical device lead comprising:
   an insulated lead body including at least one electrode;
   a helical conductor coil electrically coupled to the at least one electrode, the helical conductor coil including a plurality of turns having a coil pitch, the helical conductor coil having a circumference and an outer diameter, the helical conductor coil helically wound from one or more conductive filars each having a filar diameter, wherein the coil pitch and outer diameter are selected based on the filar diameter to minimize heating of the helically coiled conductor in the presence of an MRI field; and a polymer coil extending over the helical conductor coil and completely around the entire circumference of the helical conductor coil, the polymer coil formed by one or more polymer filars disposed coaxially around and abutted against the circumference of the helical conductor coil, wherein the polymer coil is configured to increase a torque transmitting capacity of the helically coiled conductor.

9. The medical device lead of claim 8, wherein the helical conductor coil is unifilar, and wherein the coil pitch is one to about two times the filar diameter.

10. The medical device lead of claim 8, wherein the outer diameter is at least 4.5 times the coil pitch.

11. The medical device lead of claim 8, wherein the polymer coil has a polymer coil pitch, and wherein the polymer coil pitch is less than or equal to the conductive coil pitch.

12. The medical device lead of claim 8, wherein the one or more polymer filars each has a polymer filar diameter, and wherein the polymer filar diameter is less than or equal to the conductive filar diameter.

13. The medical device lead of claim 8, wherein the one or more polymer filars of the polymer coil is wound in a direction opposite the one or more conductive filars.

14. The medical device lead of claim 8, wherein the one or more conductive filars have a diameter between 0.0005 and 0.011 inches.

15. A conductor assembly for a medical device lead, the conductor assembly comprising:
   a helical conductor coil including a plurality of turns having a conductive coil pitch, the helical conductor coil wound from one or more conductive filars each having a conductive filar diameter, the helical conductor coil having a circumference; and
   one or more polymer coils each including one or more polymer filars disposed over and coaxially around the entire circumference of the helical conductor coil and abutted against the circumference of the helical conductor coil, wherein the one or more polymer coils are configured to increase a torque transmitting capacity of the helical conductor coil.

16. The conductor assembly of claim 15, wherein the helical conductor coil is unifilar, and wherein the conductive coil pitch is one to about two times the conductive filar diameter.

17. The conductor assembly of claim 15, wherein the one or more polymer coils each have a polymer coil pitch, and wherein the polymer coil pitch is less than or equal to the conductive coil pitch.

18. The conductor assembly of claim 15, wherein the one or more polymer filars each has a polymer filar diameter, and wherein the polymer filar diameter is less than or equal to the conductive filar diameter.

19. The conductor assembly of claim 15, wherein the one or more polymer filars of at least one of the one or more polymer coils are wound in a direction opposite the one or more conductive filars.

20. The conductor assembly of claim 15, wherein the one or more polymer coils comprises two polymer coils wound in opposite directions.

* * * * *